United States Patent [19]
Heimke et al.

[11] 3,939,497
[45] Feb. 24, 1976

[54] FASTENING MEANS FOR HIP JOINT PROSTHESIS SOCKETS

[75] Inventors: Günther Heimke, Mannheim; Peter Griss, Plankstadt; Hanns Von Andrian-Werburg, Ilvesheim; Herbert Heil, Edingen; Paul Wachter, Mannheim, all of Germany

[73] Assignee: Friedrichsfeld GmbH. Steinzeug-und Kunstoffwerke, Mannheim, Germany

[22] Filed: Dec. 9, 1974

[21] Appl. No.: 530,553

[30] Foreign Application Priority Data
Dec. 28, 1973 Germany............................ 2365022

[52] U.S. Cl................................. 3/1.912; 128/92 C
[51] Int. Cl.² ............................................ A61F 1/24

[58] Field of Search.......................... 3/1, 1.9–1.913; 128/92 C, 92 CA; 32/10 A

[56] References Cited
UNITED STATES PATENTS
2,857,670   10/1958   Kiernan............................ 128/92 C
FOREIGN PATENTS OR APPLICATIONS
2,096,895   3/1972   France............................... 128/92 C Primary Examiner—Ronald L. Frinks

[57] ABSTRACT

A socket for hip joint prosthesis is secured to a cavity in the bone tissue by a series of radially arranged pegs which can be projected outwardly from the wall of the socket into the surrounding tissue by a central screw member which also has a self-tapping thread which also enters the tissue.

5 Claims, 5 Drawing Figures

FASTENING MEANS FOR HIP JOINT PROSTHESIS SOCKETS

This invention relates to the socket part of a total hip joint prosthesis, that is to say to that part of the prosthesis which is inserted into the hip bone amd more particularly, to the case in which the insertion of the prosthesis into the hip bone takes place without the use of a bone cement. For implantation without the use of a cement, only those parts of a prosthesis which consist of a bio-inert raw material are involved, which permits the intimate and mechanically firm growing of the bone tissue onto the surface of the prosthesis at the places provided therefor. Therefore, the invention relates to sockets for total hip joint prostheses made of a biologically-inert material, especially of a dense $Al_2O_3$ ceramic.

Hitherto total hip joint prostheses were attached in orthopedic surgery essentially with the aid of plastic bone cement in the bone cavities adjoining the joint. This technique has been used for about 10 years to a large and continuously growing extent. However, it has turned out, that the use of plastic bone cement leads to various complications. The possibility of cement free implantation of the two parts of a hip joint prosthesis, namely of the socket part to be attached in the hip bone and the thigh part attached in the femur, therefore represents an essential and significant progress.

The customary and hitherto available sockets for hip joint full prostheses for implantation with the aid of bone cement cannot be adapted easily for the cement free implantation, since a certain time in the order of magnitude of 1–3 months is needed for the growing in or growing on of the tissue to the surface of the prosthesis. During this time, a relative movement between the bone tissue and the socket must be avoided. However, this avoidance of relative movements between the bone tissue and the side of the socket facing it has not been ensured in the case of these former socket constructions.

Socket constructions have already been proposed, made of aluminum oxide ceramic in a dense and/or porous form, or with a porous layer on the surface facing the bone, which are intended for a cement free implantation (German published application No. 2,134,316). It turns out however, that such sockets are not protected sufficiently against twisting.

Socket constructions for cement free implantation have also already been proposed, which have a protection against twisting and which in their entirety, consist of a raw material, which makes possible a mechanically firm growing on of the bone tissue to the surface of the prosthesis. In the copending application corresponding to German application No. 2314175, a socket for hip joint prosthesis made of aluminum oxide ceramic which can be screwed in, has been described. While this latter prosthesis represents an advance as compared to the then status of the prior art, since by screwing in with a partially self-tapping thread and with the attachment of additional protection against twisting, a stable seat of the socket immediately after the operation is assured, yet the expense in the use of this socket is quite high, because of the necessity of precutting of the thread and predrilling of the holes for the twist prevention.

A socket part of a full hip joint prosthesis has also been proposed in which case the twist prevention is given by the angular shape of the side of the socket facing the hip bone (copending application corresponding to German application No. 2325585). In that case, a socket made of $Al_2O_3$ ceramic, it is true that the necessary instruments needed for threading and predrilling of the holes serving for prevention of twisting is no longer necessary and a number of operations are saved during implantation. Nevertheless, it turned out that it is quite difficult to achieve, under the conditions of the operation, a high degree of precision in chiselling the shape of the angular socket out of the hip bone, which is required for a firm solid seat for the socket.

The socket, according to the present invention, for hip joint prostheses for cement free implantation, results in a further simplification of the technique of the operation and thus constitutes a notable advance, as compared to the hitherto known socket constructions.

Figure 1:
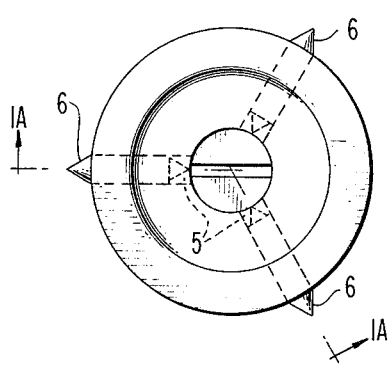
FIGS. 1 and 1A are plan, and elevational, views of a preferred socket.
Figure 1A:
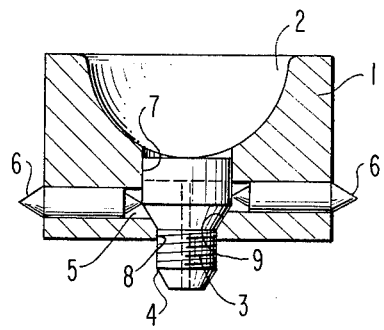

In FIGS. 1 and 1A of the drawings, the reference numeral 1 represents the essential cylindrical body of the socket in its outside contour. In it, an approximately semispherical cavity 2, is provided in one of its two sides in which the head of the femur part of the hip joint prosthesis is mounted after insertion. The socket in its center is provided with two concentric bores having variable diameters 7 and 8, with a tapered shoulder 9 between them into which the screw 3 fits. The screw 3 at its lower end has a thread 4. The body 1 of the socket contains bores which are designated by numeral 5. The pegs 6 are mounted in them.

Figure 2:
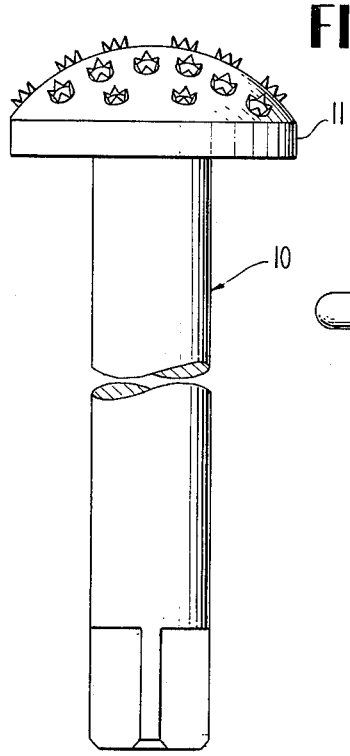
FIGS. 2 and 2A are elevational, and plan, views of an implanting tool.
Figure 3:
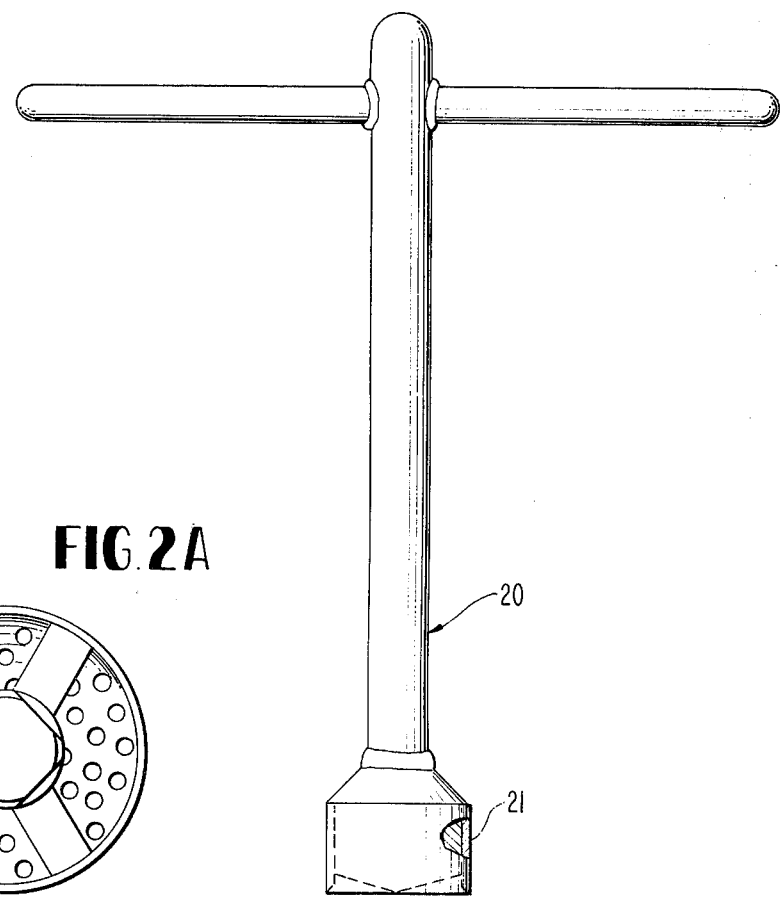
FIG. 3 shows another such tool.
Figure 2A:
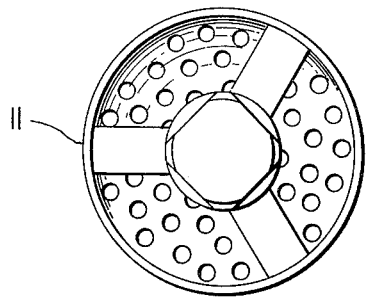

The procedure for the implantation of the hip joint socket according to the invention is as follows: First of all, the implantation space in the hip bone is preshaped with a rasp 10 as shown in FIGS. 2 and 2A, which is similar to a cutter head. The outside diameter of this cutter head 11 corresponds to the outside diameter of the socket 1. Subsequently the hollow space needed for the socket is finished in the hip joint bone with an instrument 20, having a hollow cutter 21 to make the space cylindric¹ as shown in FIG. 3. Finally, the hole needed for the central screw 3 in socket 1 is drilled in the center by means of a drill limited correspondingly in its drilling depth to such a point, that the thread 4 can later penetrate in a self-tapping manner.

During insertion of the socket, the screw 3 is in an unscrewed state to such a point that the peg 6 will be in contact with the lower course of the thread 4 in the lower part of the screw 3. This portion of the screw 3, carrying the thread, has a smaller diameter than its upper part, so that the pointed inner ends of the pegs 6 upon engagement with the turns of the thread 4, do not project from the sides of the body 1 of the socket. In order to make possible the engagement of the inner pointed ends of the pegs 6 in the lowest turn of the thread 4 on screw 3, the bores in which the pegs 6 are guided, are displaced radially outwardly into the surrounding bone tissue. As drawn in FIG. 1, three pegs are arranged radially and the corresponding bores are displaced by 120° and are differentiated as to their height in each case by one third of the height of the pitch of the thread. After insertion of the socket, the screw 3 is screwed in with a screwdriver. In the case of this screwdriver, the part touching the screw, and preferably the socket, is covered with plastic in order to avoid metal abrasion of the socket or its parts. During this screwing in of the screw 3, the pegs 6 first serve for the guidance of the screw and they constitute the support for driving them in. After penetration of the screw 3 into the corresponding predrilled part of the hip bone, the thread is tapped there automatically in the same way a wood screw acts. At the same time, the pegs 6 are forced apart because of the ending of thread 4 and by contact with the tapered shoulder defined by the transition part of the screw 3 between the area of smaller diameter to the superposed part of larger diameter. The pointed ends of the pegs 6 directed outwardly at the same time penetrate the hip bone and lead to the necessary firm and twistproof anchoring of the socket in the hip bone. Also, as the screw moves down, the tapered shoulder meets the shoulder 9 defining the transition between the two bores 7 and 8, which assists in retaining the socket in place.

With this implantion technique, which is made possible by the socket according to the invention, there is achieved with a few manipulations, a mechanically firm and twistproof seat for the socket. At the same time, there is no great requirement for precision to be made for the preliminary work of drilling out the space in the hip bone required for the socket, so that an efficient procedure is also possible for these preparatory operations. However, the saving of time in such a serious operation as represented by the insertion of a total hip joint prosthesis, is a decisive factor and constitutes an essential criterion for the useability of an implant.

The preferred material for a socket for total hip joint prostheses according to the invention consists of a raw material which permits the mechanically firm adhesion, or growing on, of bone tissue to the surface of the implant. Preferably, all individual parts of the socket, according to the invention, are made of the same raw material. The mechanically tight and firm "growing on" of bone tissue exists particularly in the case of aluminum oxide ceramic. Some glass ceramic types also fulfill this condition. However, aluminum oxide ceramic, because of its other mechanical characteristics, especially because of its high wear resistance, is preferred for this use. By aluminum oxide ceramic, one understands a ceramic material, which consists of more than 85 percent of aluminum oxide. For hip joint prostheses and the sockets according to the invention, an aluminum oxide ceramic with more than 96 percent $Al_2O_3$ is preferred. A highly corrosion resistant and a highly wear resistant aluminum oxide ceramic with more than 99 percent aluminum oxide contents is particularly favorable. These materials are used in a state sintered to high density, that is to say, having a density of at least 90 percent, preferably 95 percent of the theoretical density of the material used.

We claim:

1. A socket for hip joint prosthesis for cement free implantation comprising a body of biologically inert material provided with a semi-spherical concentric bearing cavity, a series of pegs longitudinally slidably mounted in said body in space relation to each other, a threaded screw mounted for axial movement in a concentric bore provided in said body for operative engagement with one end of each of said pegs, the threads being disposed on one end of the screw for self-tapping engagement with the tissue of the bone, a portion of the screw remote from said one end being of larger diameter than the threaded portion to define an annular shoulder, said bore having a portion of reduced diameter defining an annular shoulder for engagement with the first mentioned shoulder for assisting in holding the body in place.

2. The invention defined in claim 1, wherein all of the components are composed of dense $Al_2O_3$ ceramic.

3. The invention defined in claim 1, wherein said pegs are mounted in a series of passages radiating outwardly from said bore.

4. The invention defined in claim 3, wherein the inner ends of said pegs are provided with surfaces which are contoured for operative engagement with said screw threads during the initial rotation of said screw, said pegs being forced outwardly by engagement with said first mentioned shoulder when said threads are in engagement with bone tissue.

5. The invention defined in claim 1, wherein said body is cylindrical.

* * * * *